United States Patent [19]
Jamshidi

[11] Patent Number: 5,807,275
[45] Date of Patent: Sep. 15, 1998

[54] BIOPSY NEEDLE

[75] Inventor: Khosrow Jamshidi, St. Paul, Minn.

[73] Assignee: Medical Biopsy, Inc., Minneapolis, Minn.

[21] Appl. No.: 504,193

[22] Filed: Jul. 19, 1995

[51] Int. Cl.⁶ .................................................. A61B 10/00
[52] U.S. Cl. .......................................... 600/567; 606/170
[58] Field of Search ..................... 128/751, 753, 128/754; 606/167, 170

[56] References Cited

U.S. PATENT DOCUMENTS

| | | | |
|---|---|---|---|
| 4,655,226 | 4/1987 | Scarfone et al. | 128/754 |
| 4,793,363 | 12/1988 | Ausherman et al. | 128/754 |
| 5,368,046 | 11/1994 | Lee | 128/754 |

OTHER PUBLICATIONS

"Form and Function Go Hand in Hand", ©1994 Baxter Healthcare Corporation.

"Bone Biopsy Needles Reduced Patient Trauma with No–Drift Needle Design" p. 7A–4 from E–Z–EM Retail Price List, May 1, 1994.

"Bone Biopsy", p. 19, Bard Radiology Hospital Price List, Aug. 1993.

"'I' Type Sterile Single Use Biopsy Needle", Bone Marrow Aspiration/Biopsy Needle, Manan Medical Products, Inc., Mar. 1990.

"'J' Type Sterile Single Use Biopsy Needle", Bone Marrow Aspiration/Biopsy Needle, Manan Medical Products, Inc., Mar. 1990.

"Monoject® Bone Marrow Biopsy Needles and Trays", Bin #7035, Product Profile, Nov. 1990.

"Sterile, Single–Use B–D Bone Marrow Biopsy Needle Designed for Biopsy of the Iliac Crest", Reorder No. 8627, Special Procedures and Radiology/Biopsy Products Catalog, Becton Dickinson, 1993.

*Primary Examiner*—Max Hindenburg
*Assistant Examiner*—Pamela L. Wingood
*Attorney, Agent, or Firm*—Nawrocki, Rooney & Sivertson, P.A.

[57] ABSTRACT

A biopsy needle assembly and kit for acquiring a sample of tissue and method of using the same. The biopsy needle assembly includes a needle having a lumen extending therethrough and a stylet sized to extend through the lumen. A divided ergonomically shaped handle has a distal part formed around the proximal end of the needle and a proximal part formed around the proximal end of the stylet. These parts can be locked together, but only from a single right angle initial orientation with a rotation in one direction only from there to lock the two parts together. A stop ensures locked alignment. Locking the handle parts in alignment provides a known orientation between the distal ends of the needle and stylet. A Luer connector attached to the proximal end of the distal handle part is exposed only when the handle parts are disconnected for connecting either a plug or aspiration apparatus.

2 Claims, 3 Drawing Sheets

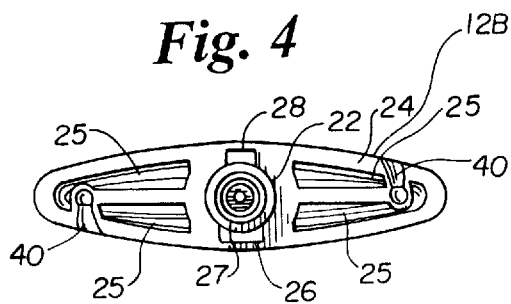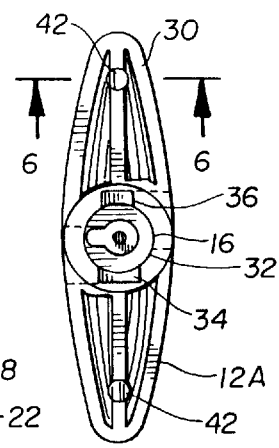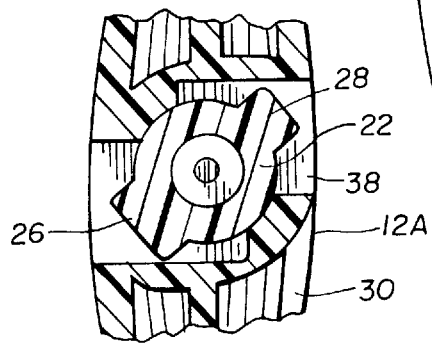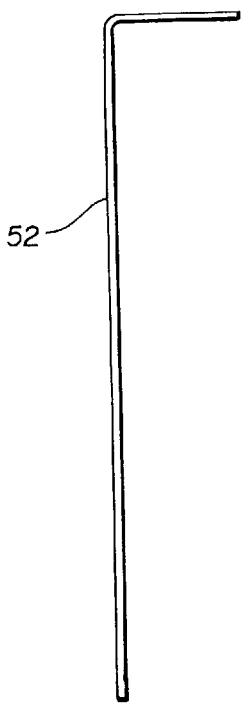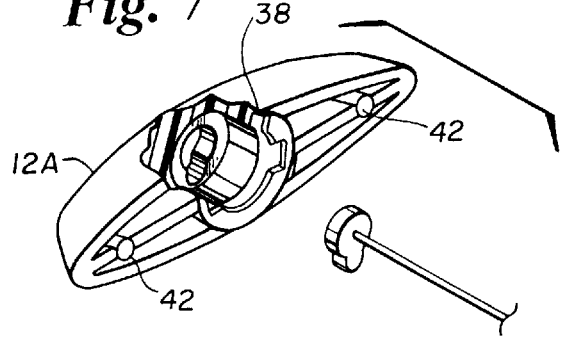

BIOPSY NEEDLE

The present invention relates to biopsy needle equipment for acquiring samples of body specimens from a living patient.

DESCRIPTION OF THE PRIOR ART

Biopsy needle equipment is available which locks a stylet to a needle and which also provides some means of connecting a plug or aspirating equipment to the proximal end of the needle lumen. The problem with this equipment has been that secure attachment of the stylet to the needle is not provided, and that a connector for a plug or aspirating equipment normally extends proximally from a handle used to force the needle and stylet through tissue. The first presents a considerable problem since a great deal of force must be exerted on the stylet and needle when bone is penetrated. The second presents a problem in exerting this force since the connector is opposite the hand which makes generating a considerable amount of force uncomfortable, if not impossible.

The instant invention overcomes the first problem by dividing the handle used for exerting force into proximal and distal parts which can be attached securely together but separated readily. The handle parts are attached respectively to the needle and the stylet which results in these parts also being attached securely together. The second problem is solved by having a Luer connector, mounted within the handle and connected to the needle lumen, exposed only when the handle parts are separated. These handle parts provide an ergonomically shaped handle only when required and are separated after penetration.

SUMMARY OF THE INVENTION

The present invention is a device for acquiring a sample of tissue or fluid from a patient, generally referred to herein as a biopsy needle assembly. The invention may also be packaged as a kit which includes all necessary components for performing sampling of tissue. The invention also includes a method for utilizing the device of the present invention in acquiring the biopsy, fluid or tissue sample. The biopsy needle assembly is specifically designed to include features which prevent the loss of any portion of the tissue or fluid sample during extraction of the biopsy needle from the incision track after a sample has been captured within the lumen of the needle or remove a sample by aspiration. Thus, the biopsy needle assembly includes a concealed male portion of a Luer connector to sealingly receive a mating plug or aspiration apparatus.

Entering a biopsy needle through bone into bone marrow requires that a great deal of force be exerted on the needle by the physician. This is greatly facilitated here by an ergonomically shaped handle which closely fits the hand and permits generating a great deal of force against the needle with the force being optimally distributed.

The biopsy assembly includes a handle, a stylet and a needle with a lumen extending from the distal to the proximal end being sized to accept the stylet. The handle is formed of two parts, a proximal part and a distal part. The opposing surfaces of the handle parts are generally planar. The proximal handle part is attached to the proximal end of the stylet, and the distal handle part is attached near the proximal end of the needle. When the stylet is inserted into the needle lumen, the planar handle surfaces face each other.

An extension, shaped like a cylinder wit h a proximal planar surface, is formed around the proximal end of the needle and attached extending proximally from the planar surface of the distal handle part. The extension has two outwardly extending opposed flanges of different widths, offset from but lying in the plane of the extension proximal end. A male Luer connection, attached to the proximal end of the extension and around the needle, extends proximally from the extension.

A cylindrical shaped recess into the planar distal surface of the proximal handle part is sized to accept the proximally projecting extension and Luer connector extension. This recess has wings of opposed outward unequal width extensions sized to mate with and receive the opposing flanges, when the extension is placed within the recess with the handle parts in a single orientation with respect to each other. The unequal width flanges and mating unequal width wings provide only this single orientation, where the extension and flanges can be inserted into the recess and its wings. This single orientation occurs when the handle parts are at right angles to each other.

Two slots, each beginning at a wing, extend outwardly around the recess in the same direction approximately one-quarter of the distance around the recess circumference. The slots are located such that each is aligned with the edge of the adjacent flange, when the extension and flanges are placed within the recess and wings with the handles at the required right angle relationship. Each slot is made wide enough to receive the edges of the adjacent flange, and deep enough to permit rotation of the flange through the slot. Since each slot extends in only one direction around the recess circumference from its respective wing, the two handle parts can only be rotated in one direction relative to each other. Since the slots extend around the recess about one-quarter of the recess circumference, this permits rotating the two handle parts from the insertion right angle orientation into alignment. The terminus of each slot also extends through the side of the handle to permit observation of alignment.

Restricting the final angular relationship of the two parts to one aligned angle of the handle parts is important, because the distal end of the stylet and needle may be inclined. If they are inclined, then the orientation of the stylet with respect to the needle must be fixed so the inclination angles will match each other.

Stops are provided to ensure that the handle parts are locked in alignment. The stops are provided by two studs and two arcuate grooves. The studs project distally from the planar surface of the proximal handle part near each end. These studs engage arcuate grooves in the proximal planar surface of the distal handle part, which are formed to be in the path of the studs when the two parts are rotated with respect to one other. These arcuate grooves extend only far enough to permit rotation of the two handle parts into alignment.

After the two handle parts are locked together in alignment they form a complete ergonomically shaped handle, which permits the surgeon to exert greater force. In use, the handle parts are gripped in one hand. Being gripped together assures that the two handle parts stay in alignment and locked together in use.

The handle parts are attached before forcing the needle and stylet through the bone, since this requires a great deal of force. After forcing the needle and stylet through the bone the male Luer connector extension is then exposed by removing the stylet from the needle after merely rotating the two handle parts in the proper direction to right angles to each other. This permits attaching a plug, which mates with the Luer connector, and is provided for sealing the needle lumen before removing the sample. This improves this procedure by blocking air flow. Aspiration apparatus can also be attached to the male Luer connector instead of the plug in order to aspirate the sample.

A Luer attachment connector, of necessity, has a relatively sharp end which is covered here by an ergonomically shaped handle. This ergonomic handle shape greatly increases the force that can be generated by the physician because the resulting close hand match distributes the applied force more evenly. Locating an attachment means for a plug or aspirating apparatus within the handle provides an attachment capability for a plug or aspirating apparatus without changing this optimum ergonomic handle shape. In addition, this method of attachment provides a secure attachment of the stylet to the needle with known orientations between the two to permit using inclined distal ends on these parts. However, since the handle parts are readily separable, this attachment capability is provided with a minimum of operator inconvenience.

BRIEF DESCRIPTION OF THE DRAWINGS

In the drawings, in which like reference numerals indicate corresponding parts or elements of preferred embodiments of the present invention throughout the several views:

FIG. 4 is a top plan view of biopsy needle and distal handle part with the distal handle part removed;

FIG. 5 is a bottom plan view of the proximal handle part with the distal handle part removed and the needle in place inside the distal handle part;

FIG. 6 is a fragment of the handle parts in cross-section showing only the extension from the distal handle part and the mating and adjacent portions of the proximal handle part;

FIG. 7 is a view of the proximal handle part and needle with a cut-out to show the interior construction;

FIG. 11 is a side view of the probe.

DETAILED DESCRIPTION OF THE INVENTION

Detailed embodiments of the present invention are disclosed herein. It is to be understood, however, that the disclosed embodiments are merely exemplary of the present invention which may be embodied in various forms. Therefore, specific details disclosed herein are not to be interpreted as limiting, but rather as a basis for the claims and as a representative basis for teaching one of skill in the art to variously practice the invention.

Figure 1:
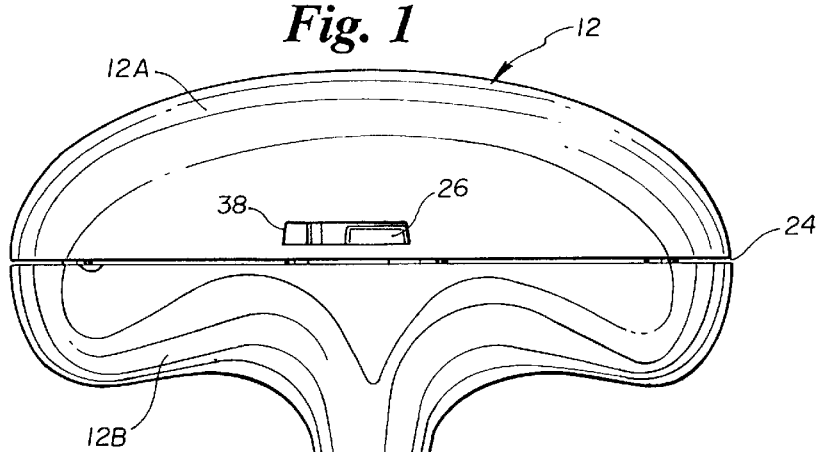
FIG. 1 is a front elevational view of the invention.

Referring now to FIG. 1 a front elevational view of a biopsy needle assembly 10 is shown. Assembly 10 uses a two part handle 12 consisting of a proximal handle part 12A and a distal handle part 12B which together form a complete handle. Proximal handle part 12A is formed around the distal end of stylet 14, and distal handle part 12B is formed around biopsy needle 16 near the distal end. As depicted here, stylet 14 is shown extending beyond needle 16 through a lumen 18, not shown, in the needle which extends from the distal to the proximal ends of the needle. The extension of stylet 14 beyond needle 16 provides a distal cutting surface 20.

Figure 3:
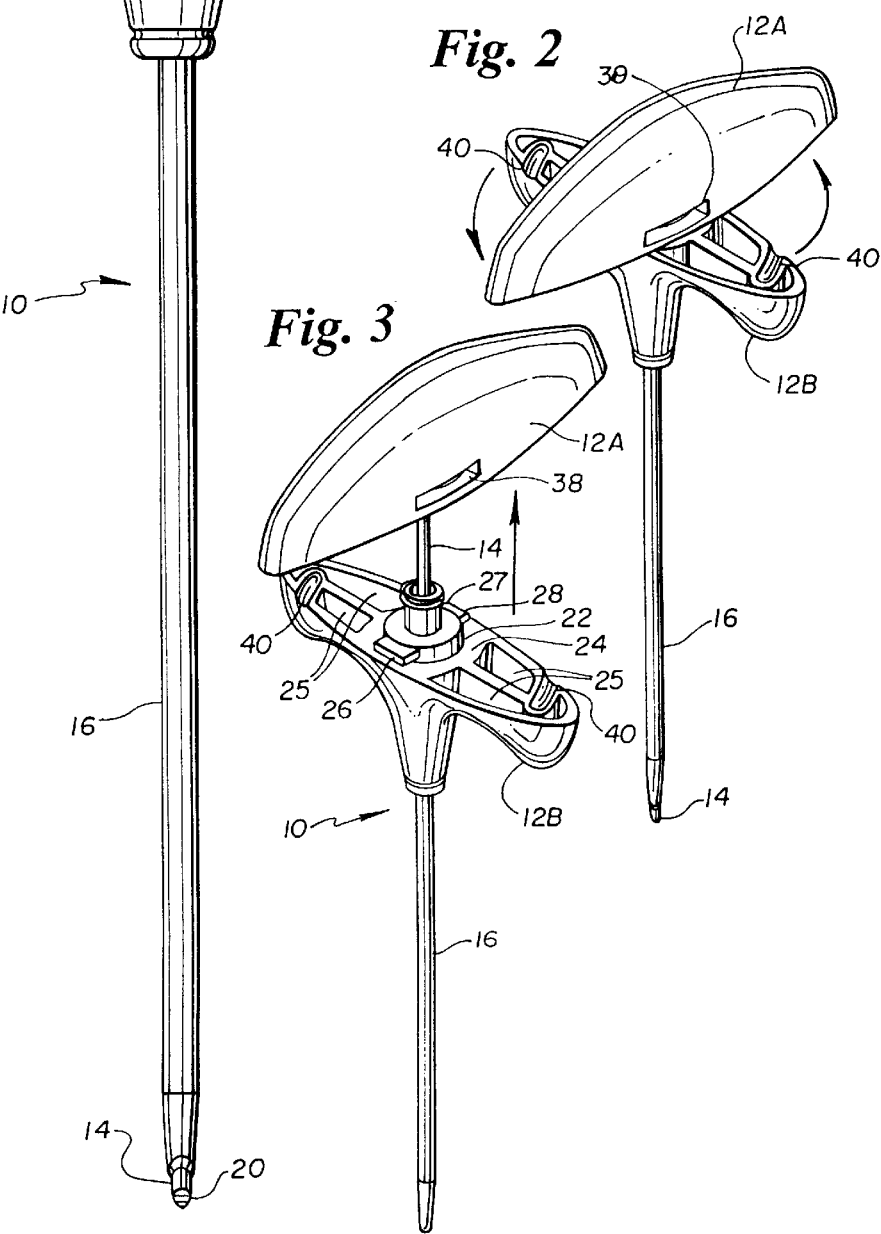
FIG. 3 is an exploded perspective view.
Figure 8:
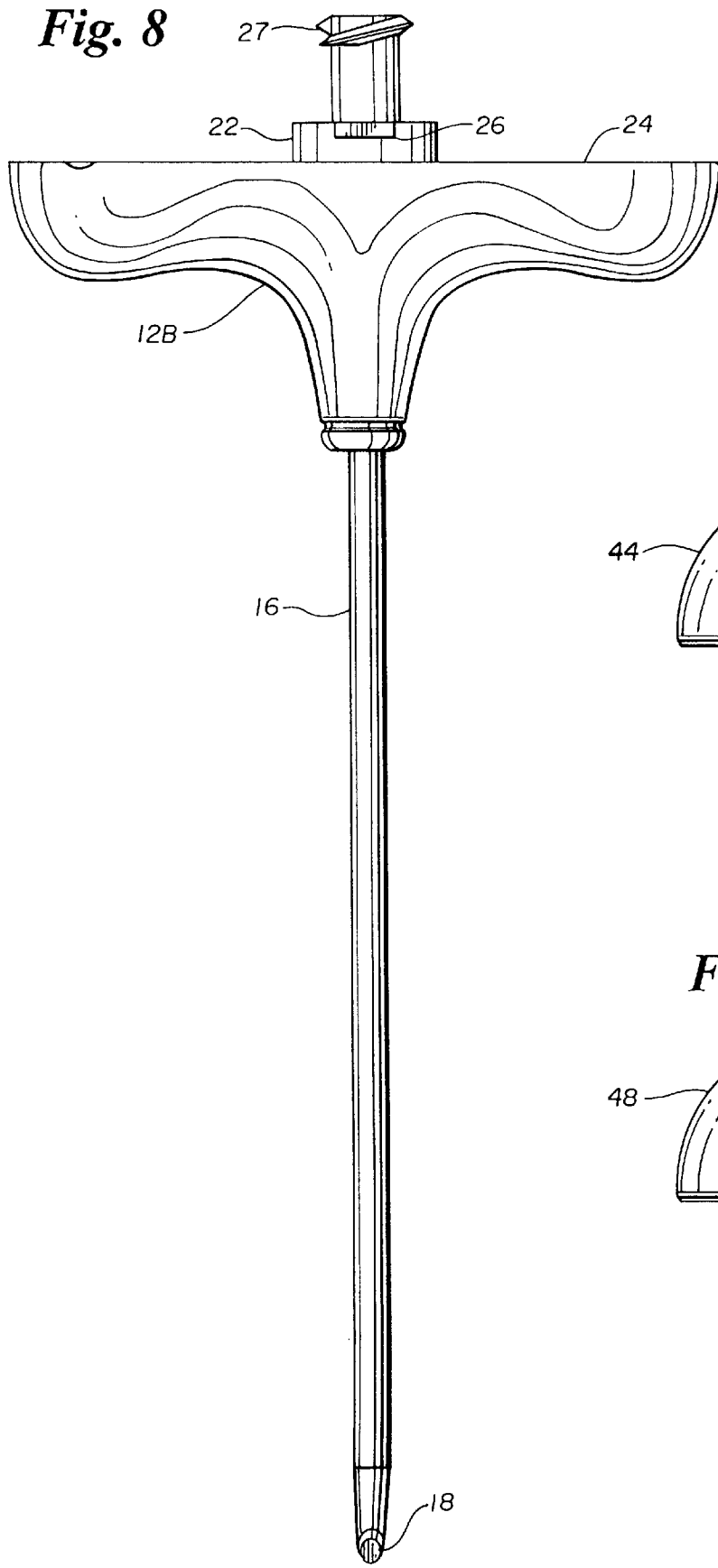
FIG. 8 is a front elevational view of the invention with proximal handle part and needle removed.

In FIG. 3, an exploded perspective view of assembly 10, shows proximal handle part 12A rotated 90 degrees from alignment with distal handle part 12B, and with stylet 14 partially withdrawn from needle 16. In FIGS. 3, 4, and 8 a cylindrical shaped extension 22 formed around the distal end of needle 16 extending proximally from surface 24 of distal handle portion 12B is shown. A wide flange 26 and a narrow flange 28 extend outwardly from extension 22 offset from and generally parallel with the proximal end of extension 22. A male Luer connector 27 is attached proximately to the proximal end of extension 22 and around needle 16. Four voids 25, into distal handle part 12B from surface 24, are provided for weight reduction. Except for a stop to be described later and the above described features surface 24 is planar.

In FIG. 5 proximal handle part 12A is shown. Distal surface 30 of proximal handle part 12A is also shown with a cylindrically shaped recess 32 extending proximally inward. Wing 34 and wing 36 are outward extensions of recess 32 with wing 34 being wider than wing 36. Recess 32 is sized to accept extension 22 and wings 34 and 36 are sized to accept flanges 26 and 28 respectively when stylet 14 in inserted through needle 16 with the orientation shown in FIG. 2. only in this orientation is wide flange 26 opposite wide wing 34 and narrow flange 28 opposite narrow wing 36 to permit inserting stylet 14 completely into needle 16.

In FIG. 7, one of the two opposed slots 38 which extend around approximately one-quarter of the circumference of recess 32 and outwardly therefrom is shown. Slots 38 are aligned with flanges 26 and 28 when extension 28 is inserted fully into recess 42 and are wide enough to accept the flange edges. These opposed slots 38 begin at the sides of wings 34 and 36 respectively and at opposite sides of recess 42. The terminus end of slots 38 extend outward through proximal handle part 12A to provide a visual indication of alignment as shown in FIG. 1. Slots 38 permit rotating distal handle part 12A with respect to proximal handle part 12B one-quarter of a turn into alignment but only in the slot direction. FIG. 6 shows flange 28 rotating into one of the slots 28. While flanges 26 and 28 are offset the same amount here, this is not a requirement, since slots 38 can be offset different amounts to match unequal offsets of flanges 26 and 28. This engagement of flanges 26 and 28 with slots 38 locks distal handle part 12B securely to proximal handle part 12A, which also locks attached stylet 14 securely within needle 16.

Figure 2:
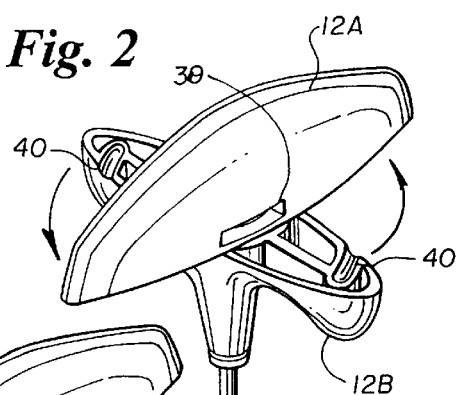
FIG. 2 is a perspective view.

FIGS. 2, 3 and 4 show arcuate grooves 40 in surface 24 of distal handle part 12B. FIGS. 5 and 7 shows studs 42 which extend distally from proximal handle part 12A. When stylet 14 is inserted through lumen 18 completely into needle 16, as shown in FIG. 2, and proximal handle part 12A rotated into alignment with distal handle part 12B, as shown in FIG. 1, studs 42 will engage and track grooves 40 to their terminus when the two handle parts are aligned. This provides a stop to ensure that the handle parts 12A and 12B are aligned at the end of this rotation. If the angle between handle parts 12A and 12B were reversed 180 degrees, then studs 42 would be opposite the closed ends of grooves 40 which would prevent insertion. This reversal is prevented by the different widths of wings 34 and 36 and of flanges 26 and 28 described earlier.

Figure 9:
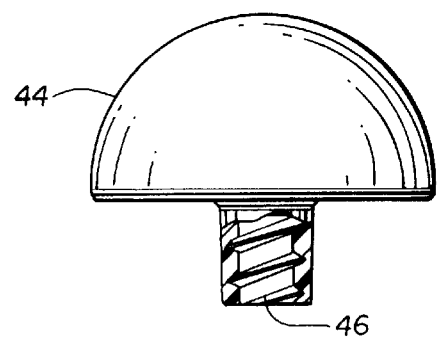
FIG. 9 is a side elevational view of a plug.
Figure 10:
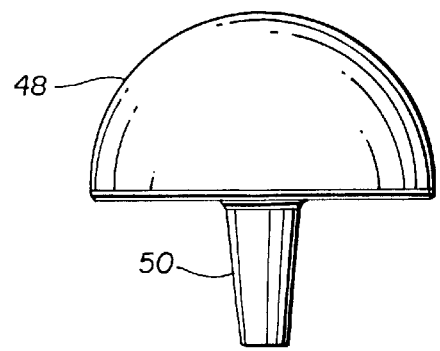
FIG. 10 is a side elevational view of an alternative embodiment of the invention.

FIG. 9 shows plug 44 with a female Luer connection 46 and FIG. 10 shows plug 48 with a stopple end 50. Female Luer connection 46 of plug 44 is sized and arranged to mate with male Luer connector 27. Stopple 50 of plug 48 is sized and shaped to wedge within and stopple the proximal opening of male Luer connector 27. If desired, when plug 52 is used, male Luer connector can be replaced by a simple cylinder.

FIG. 11 shows probe 52 which has a circular cross-section sized to slidingly fit within lumen 18 of needle 16. Probe 52 has a length greater than needle 16 and distal handle part 12B together to permit removing specimens from within the needle In use, this biopsy needle apparatus 10 can aspirate marrow material as well as take biopsy specimens. The arrangement is such that it is particularly adapted to obtaining specimens from the patient's iliac crest.

In the procedure of obtaining specimens from a patient's iliac crest, typically a skin incision is made using aseptic techniques and an incision made with a scalpel blade in the appropriate area. Biopsy needle assembly 10 is assembled as shown in FIG. 1, with proximal handle part 12A locked to distal handle part 12B as described earlier, to provide a complete ergonomically shaped handle for the physician and a distal cutting surface 20 for penetrating bone.

An incision is then made and handle 12 of biopsy needle apparatus 10, held in the hand between the thumb and fingers and braced against the juncture of the thumb and forefinger, is introduced through the incision and brought in contact with the posterior iliac spine. The needle 16 is then rotated in a alternating clockwise counterclockwise direction by handle 12 and simultaneously entered into the iliac spine by exerting force against the handle while pointing the needle in the direction of the anterior superior iliac spine.

Lower resistance to needle 16 is felt once the needle enters the marrow cavity whereupon proximal handle part 12 and attached stylet 14 is removed by rotating the two handle parts 12A and 12B in the proper direction relative to each other until the two parts are 90 degrees to each other to the attitude shown in FIG. 2. This removes flanges 26 and 28 from slots 38 and unlocks the two handle parts 12A and 12B from each other. Proximal handle part 12A and attached stylet 14 is then removed from apparatus 10 to expose male Luer connector 27 as shown in FIG. 3.

For aspiration procedures, aspirator apparatus having a female Luer connector, is then attached to male Luer connector 27 and this procedure accomplished.

For biopsy procedures, needle 16 is slowly advanced millimeter by millimeter by firm pressure on distal handle part 12B, using alternating clockwise and counterclockwise rotation, to advance the needle into the marrow two to three centimeters or until adequate marrow sample is obtained. The force required for this and subsequent operations is not as great as that for the previous part of these procedures, and therefore the proximal handle part 12A is not required since an ergonomically shaped handle is no longer required.

Alternatively, to remove needle 16 with the biopsy specimen lodged in lumen 16 distal handle part 12B is used to manipulate the needle. In this procedure needle 16 is first pulled back two to three millimeters and its tip then redirected with gentle pressure to push it into the marrow cavity the same distance that it was pulled back; second, the needle is rotated several times in alternating clockwise and counterclockwise rotations to secure the specimen in lumen 18 of the needle. At this time either plug 44 is used to close the proximal end of lumen 18 at male Luer connector 27, or plug 48 is inserted in the Luer connector as a stopple. This permits removing needle 16 with the specimen remaining secure because air is not permitted to enter lumen 18. Needle 10 is then removed from the patient's ilium very slowly and in a rotary fashion to avoid losing the specimen using distal handle part 12B. After removal from the ilium, the specimen is removed from lumen 18 by introducing probe 52 into lumen 18 through the distal end of needle 16, and pushing the specimen out of the proximal end. Use of a different method than this may crush the specimen and make it undesirable for interpretation.

While this invention has been described with respect to specific embodiments, these description are not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

I claim:

1. A biopsy needle assembly, comprising:

(a) an elongated needle having a proximal end and a distal end, and having a lumen extending between said proximal end and said distal end;

(b) an elongated stylet having a proximal end and a distal end;

(c) a handle of a predetermined shape divided into two parts, having a proximal handle part with a distal surface formed around the proximal end of said stylet, and having a distal handle part with a proximal surface formed around said needle near the proximal end thereof, said stylet being removably positionable within said needle lumen through said distal handle part;

(d) locking apparatus formed from, and integral with, said proximal handle part arranged to attach and lock said proximal handle part to said distal handle part with said stylet positioned within said lumen, with said distal surface of said proximal handle part adjacent to said proximal surface of said distal handle part, and such that said handle parts can be rotated into alignment with each other, said locking apparatus comprising an extension from the proximal surface of said distal handle part around the proximal end of said needle, and a mating recess in the distal surface of said proximal handle part, said extension being generally cylindrical in shape with an axis coaxial with said needle lumen, said extension having opposed flanges of unequal annular widths extending radially outwardly therefrom generally perpendicular to said axis, said flanges each being a predetermined distance from a proximal end of said extension, said recess being generally cylindrical in shape with an axis generally aligned with said stylet, said recess having opposed unequal width wings extending outwardly therefrom generally perpendicular to said axis, said wings being sized and arranged such as to receive said flanges but only when said extension is inserted into said recess with said handle parts at a predetermined angle relationship with respect to one another, said recess further having opposed slots extending outwardly therefrom and generally perpendicular to the recess cylindrical axis, said slots each having an entrance end from an adjacent wing and an opposite terminal end approximately one quarter of the recess circumference therefrom, said slots having a size and path such that when said extension is inserted into said recess with said handle parts at said predetermined angle relationship with respect to one another, each flange will be opposite an adjoining slot and each flange can enter and traverse the adjoining slot as said handle parts are rotated in a predetermined direction of rotation into alignment; and (e) a male connector attached to a proximal side of said extension around the proximal end of said needle, said recess being sized to also accept said connector.

2. A biopsy needle assembly, comprising:

(a) an elongated needle having a proximal end and a distal end, and having a lumen extending between said proximal end and said distal end;

(b) an elongated stylet having a proximal end and a distal end;

(c) a handle of a predetermined shape divided into two parts, having a proximal handle part with a distal surface formed around the proximal end of said stylet, and having a distal handle part with a proximal surface formed around said needle near the proximal end thereof, said stylet being removably positionable within said needle lumen through said distal handle part;

(d) locking apparatus formed from, and integral with, said proximal handle part arranged to attach and lock said proximal handle part to said distal handle part with said stylet positioned within said lumen, with said distal surface of said proximal handle part adjacent to said proximal surface of said distal handle part, and such that said handle parts can be rotated into alignment with each other, said locking apparatus comprising an extension from the proximal surface of said distal handle part around the proximal end of said needle, and a mating recess in the distal surface of said proximal handle part;

(e) stop apparatus formed from, and integral with, said handle parts comprising as least one stud projecting from the distal surface of said proximal handle part and an opposing arcuate groove having an entrance end and a terminus end, said stud and said groove being arranged such that when said extension is positioned within said recess in a predetermined angle relationship and said handles rotated in a predetermined direction, said stud will engage and mate with said groove until said stud reaches the terminus end of said groove; and (f) a male connector attached to a proximal side of said extension around the proximal end of said needle, said recess being sized to also accept said connector.

\* \* \* \* \*